United States Patent
Peng et al.

(10) Patent No.: US 11,910,768 B2
(45) Date of Patent: Feb. 27, 2024

(54) **METHOD FOR BREEDING A NEW VARIETY OF HIGH-QUALITY *GOSSYPIUM HIRSUTUM***

(71) Applicant: COTTON SCIENCE RESEARCH INSTITUTE OF HUNAN, Hunan (CN)

(72) Inventors: Fanjia Peng, Hunan (CN); Zhigang Zhang, Hunan (CN); Yujun Li, Hunan (CN); Yongbo Wang, Hunan (CN)

(73) Assignee: COTTON SCIENCE RESEARCH INSTITUTE OF HUNAN, Hunan (CN)

( * ) Notice: Subject to any disclaimer, the term of this patent is extended or adjusted under 35 U.S.C. 154(b) by 0 days.

(21) Appl. No.: 17/776,161

(22) PCT Filed: Oct. 15, 2021

(86) PCT No.: PCT/CN2021/124094
§ 371 (c)(1),
(2) Date: May 11, 2022

(87) PCT Pub. No.: WO2022/083511
PCT Pub. Date: Apr. 28, 2022

(65) Prior Publication Data
US 2023/0225271 A1      Jul. 20, 2023

(30) Foreign Application Priority Data
Oct. 21, 2020    (CN) .......................... 202011129653.1

(51) Int. Cl.
*A01H 6/60*    (2018.01)
*A01H 1/04*    (2006.01)

(52) U.S. Cl.
CPC ............... *A01H 1/04* (2013.01); *A01H 6/604* (2018.05)

(58) Field of Classification Search
CPC .................................. A01H 1/04; A01H 6/604
See application file for complete search history.

(56) References Cited

FOREIGN PATENT DOCUMENTS

| AU | 2015271956 A1 | 7/2016 |
| CN | 102379238 A | 3/2012 |
| CN | 104221848 A | 12/2014 |
| CN | 112167054 A | 1/2021 |
| WO | 2022083511 A1 | 4/2022 |

OTHER PUBLICATIONS

Campbell et al Euphytica vol. 144, pp. 69-78 (Year: 2005).*
Cotton Seed Distributors extension and development team The Australian Cottongrower Dec. 2005-Jan. 2006, pp. 20-25 (Year: 2006).*
Xie et al Colloids and Surfaces B: Biointerfaces vol. 60, pp. 258-263 (Year: 2007).*
Sun et al Biologia vol. 68, No. 2, pp. 249-257 (Year: 2013).*
International Search Report for related International Application No. PCT/CN2021/124094, dated Jan. 14, 2022.
Zhang et al., "Research Progress on China's Transgenic Cotton and Sustainable Development Measures", Proceedings of 2005 Annual Meeting of China Cotton, Aug. 1, 2005, pp. 103-106.
Munir et al., "Heterosis and correlation in interspecific and intraspecific hybrids of cotton", vol. 15, No. 2, Jun. 24, 2016, 13 pages.

* cited by examiner

*Primary Examiner* — David H Kruse
(74) *Attorney, Agent, or Firm* — DITTHAVONG, STEINER, & MLOTKOWSKI

(57) ABSTRACT

The present invention discloses a method for breeding a new variety of high-quality *Gossypium hirsutum*, including breeding a parent Xiang 176 line, breeding parent Xiang 267, crossing and composite-crossing the Xiang 176 line and the Xiang 267 as parents, and obtaining the new variety of high-quality conventional *Gossypium hirsutum* in their offspring. The plant type of this variety was tower type, with good growth vigor in the seedling stage and the boll opening stage, good uniformity, dense stalk cilia, white anthers, smooth boll opening, stable agronomic traits, high yield, and excellent fiber quality.

6 Claims, No Drawings

US 11,910,768 B2

METHOD FOR BREEDING A NEW VARIETY OF HIGH-QUALITY *GOSSYPIUM HIRSUTUM*

CROSS-REFERENCE TO RELATED APPLICATIONS

This application is the national phase application of international application number PCT/CN2021/124094 filed on Oct. 15, 2021, which claims priority to Chinese application number 202011129653.1 filed on Oct. 21, 2020.

FIELD OF THE INVENTION

The present invention relates to a method for breeding a new cotton variety, specifically relates to a method for breeding a new variety of high-quality *Gossypium hirsutum*, and belongs to the technical field of cotton breeding.

BACKGROUND OF THE INVENTION

Domestic high-quality cotton has always been favored by the market, and the price remains high. The reason is that high-quality cotton can achieve more efficient mechanical operation, higher-quality products, and more profit margins. Every year, almost all of China's cotton import quota is used for the import of high-quality cotton. According to statistics, the cumulative import volume of Australian cotton in China from 2011 to 2015 alone reached 3 million tons, accounting for about 20% of the total global imports. The production of domestic high-quality cotton has been hit by American cotton and Australian cotton for a long time. The situation of low production capacity, insufficient supply capacity, and weak competitiveness are still difficult to improve. The high-quality cotton that meets the standards of American cotton and Australian cotton is less than 200,000 tons. In 2018, a trade dispute occurred between China and the United States, the entry of American cotton was hindered, but China's cotton still lacked competitiveness in global trade. Due to the absence of American cotton, the supply gap of high-grade cotton rapidly emerged, the confidence in market supply lacked, the sliding-duty cotton import quota continuously increased, and the imports of Indian cotton, Brazilian cotton and the like increased. In the second half of 2018, the import volume of Indian cotton alone increased by five times, reaching 5 million bales (850,000 tons). Therefore, China urgently needs to improve the supply capacity of high-quality cotton to ensure the safe and sustainable development of China's cotton industry.

SUMMARY OF THE INVENTION

Because of the above deficiencies in the prior art, the objective of the present invention is to provide a method for breeding a new variety of c high-quality *Gossypium hirsutum*, which can breed a high-quality cotton variety that has harmonious physical performance indexes such as fiber length, strength, fineness and uniformity and meets the requirements of the textile industry. In order to achieve the above objective, the technical solution used in the present invention is a method for breeding a new variety of *Gossypium hirsutum*, which is characterized in that by the following steps:

(1) breeding of Xiang 176: crossing a medium-long-staple Acala cotton line and a disease-resistant variety Xiangmian No. 18 as parents to obtain reciprocal cross $F_1$ combination seeds; then planting the reciprocal cross $F_1$ combination seeds in Hainan, and performing composite crossing to obtain composite cross $F_1$ seeds; in next 2 years, performing generation-adding planting on the composite cross $F_1$ seeds once in Changde, Hunan in summer and in Sanya, Hainan in winter each year, for a total of 4 generations, to obtain $F_5$ seeds; comparatively testing excellent individual plants of the $F_5$ seeds in Changde, and screening a strain with a better combination of quality traits and yield traits, named Xiang 176;

(2) breeding of Xiang 267: mixing $F_2$ of an existing approved variety Xiangzamian No. 13 to obtain mixed $F_1$ seeds, performing generation-adding planting on the mixed $F_1$ seeds in Changde, Hunan in summer and in Sanya, Hainan in winter each year according to the breading goal, for a total of 5 generations, to obtain $F_6$ seeds, and selecting a strain with high quality, high yield and low lint percent from the $F_6$ generation, named Xiang 267; and (3) breeding: crossing Xiang 176 and Xiang 267 as parents to obtain reciprocal cross $F_1$ seeds, then performing composite crossing on the reciprocal cross $F_1$ seeds to obtain composite cross $F_1$ seeds, performing generation-adding planting in Changde, Hunan in summer and Sanya, Hainan in winter each year, continuously adding generations according to the breading goal, and selecting an excellent strain from the $F_7$ generation, that is, a target variety.

Further, in the breeding step of Xiang 176, all individual plants are selected during the generation-adding planting, based on the criteria: fiber length not less than 32 mm, and lint percent not less than 45%.

Studies show that there is a significant negative correlation between fiber quality and lint percent, which is a balance point in the determination of breeding material characteristics and breeding goals.

Further, in the breeding step of Xiang 267, all individual plants are selected during the generation-adding planting of the mixed $F_1$ in Changde, Hunan and in Sanya, Hainan, based on the criteria: strong boll formation, fiber length not less than 30 mm, and lint percent not less than 38%.

Studies show that there is a significant negative correlation between fiber quality and lint percent, and a balance point between fiber quality and lint percent can be determined according to the characteristics of the line in consideration of high yield.

Further, in the breeding step, all individual plants are selected during the generation-adding planting, based on the criteria: high yield, fiber length not less than 31 mm, and lint percent not less than 40%.

The fiber quality and lint percent of a variety vary from year to year, so a lower standard is determined according to the breeding goal. The lint percent is one of the factors that have the greatest impact on the yield of a variety. If the bred variety has a relatively low lint percent, its test is disadvantageous, and it is very difficult to increase the yield of lint cotton.

Compared with the prior art, the present invention has the following beneficial effects: Generally, the probability of gene recombination in the single cross of two materials is lower than that of backcrossing and composite crossing. In actual breeding, some excellent traits in the selected progeny may be chimeras, which cannot be stably inherited, existing excellent traits segregation. Cotton crossing belongs to cytoplasmic inheritance (the trait after the before crossing is partial to the female parent), and backcrossing breeding is relatively effective in accurately improving a certain trait. However, in the present invention, the composite crossing of the reciprocal cross $F_1$ of the two parents fully recombines parental genes, reduces the influence of cytoplasmic inheritance, increases the probability of gene recombination, and breaks unfavorable linkage of genes, so as to select progeny materials with excellent genes of the parents according to the breeding goal. The parents Xiang 176 and Xiang X0935 are bred employing composite crossing of the reciprocal cross $F_1$.

During the breeding of the parent Xiang 267, mixing $F_2$ of Xiangzamian No. 13 also increases the probability of gene recombination, only select excellent progeny materials with excellent genes of the parents according to the breeding goal.

The plant type of the new variety selected by the method of the present invention is a tower type, with good growth vigor in the seedling stage and the boll opening stage, good uniformity, dense stem cilia, white anthers, smooth boll opening, stable agronomic traits, high yield, and excellent fiber quality.

DETAILED DESCRIPTION OF THE EMBODIMENTS

The present invention will be further described concerning specific embodiments. The following are only preferred embodiments of the present application, and any equivalent or similar replacements without departing from the inventive concept of the present application shall fall within the protection scope of the present invention. The parts not described in detail below are all carried out concerning the prior art.

Embodiment 1

A method for breeding a new variety of high-quality *Gossypium hirsutum* according to the present invention is specifically implemented according to the following steps:

Step 1. Breeding of Parent Xiang 176:

In the before summer of 2008, a medium-long-staple Acala cotton line (low yield, high quality, and low lint percent of about 38%) and a disease-resistant variety Xiangmian No. 18 (high yield, poor fiber quality, and high lint percent about 43%) as parents were crossed in Changde, Hunan to obtain reciprocal cross $F_1$ combination seeds;

In winter of 2008, the reciprocal cross combination $F_1$ was planted in Sanya, Hainan, and was composite-crossed (the quantitative traits of cotton were affected by cytoplasmic inheritance, and the traits of its progeny were partial to the female parent, so the reciprocal cross combination was composite-crossed to reduce the influence of cytoplasmic inheritance on the progeny and increase the probability of excellent gene recombination), to obtain composite cross $F_1$ seeds; From 2009 to 2010, the composite cross $F_1$ seeds were planted once a year in Changde, Hunan and Sanya, Hainan for adding generations (total 4 generations) to obtain $F_5$ seeds; In 2011, individual $F_5$ plants were planted in Changde, Hunan. According to the field performance and the seed test results last year, one of the strains was outstanding (combination of quality traits and yield traits), named Xiang 176.

The Xiang 176 had an ordinary yield, and the strain had a staple length of 32.9 mm, a micronaire value of 4.6, a specific strength of 36.5 CN/Tex, a boll weight of 6.5 g, a lint percent of 40.6%, and a seed index of 10.6 g. All individual plants were selected during the generation adding period, based on the criteria: appropriate combination with high yield (high quality and high yield were negatively correlated), fiber length not less than 32 mm, lint percent not less than 40%, and key screening for disease resistance and high-temperature resistance during planting in Changde, Hunan. The breeding process was shown in Table 1.

TABLE 1

Breeding process of parent Xiang 176 line

| Time (year) | Location | Breeding process | Breeding method |
|---|---|---|---|
| Spring 2008 | Changde, Hunan | Acala cotton × Xiangmian No. 18 (direct cross $F_1$) Xiangmian No. 18 × Acala cotton (back cross $F_1$) ↓ | Cross (reciprocal) |
| Winter 2008 | Sanya, Hainan | Direct cross $F_1$ × back cross $F_1$ ↓ | Composite cross |
| Spring 2009 | Changde, Hunan | $F_1$ ↓ | Individual plant selection |
| Winter 2009 | Sanya, Hainan | F2 ↓ | Individual plant selection |
| Spring 2010 | Changde, Hunan | F3 ↓ | Individual plant selection |
| Winter 2010 | Sanya, Hainan | F4 ↓ | Individual plant selection |
| Spring 2011 | Changde, Hunan | $F_5$ line (Xiang 176) | |

Step 2. Breeding of Xiang 267:

In winter of 2007, Xiangzamian No. 13 $F_1$ (good boll formation, high quality, poor boll opening, and low lint percent) was planted in Sanya, Hainan;

In summer of 2008, $F_2$ was planted in Changde, Hunan, and the population was mixed with sister lines (the method was emasculating one flower per plant in the afternoon of the first day, collecting all the removed stamens and putting them in a cool and ventilated place, and performing full mixing and pollination after the stamens lost pollen in the next morning, to increase the probability of excellent gene recombination), to obtain mixed $F_1$ seeds;

From 2008 to 2010, each generation was added once a year in Changde, Hunan and Sanya, Hainan (5 generations in total) to obtain $F_6$ individual seeds;

In 2011, $F_6$ strains were comparatively tested in Changde, Hunan, and one strain was outstanding, named Xiang 267.

The Xiang 267 had strong boll formation, and the strain had a staple length of 30.1 mm, a micronaire value of 4.9, a specific strength of 31.3 CN/Tex, a boll weight of 5.8 g, a lint percent of 38.2%, and a seed index of 10.9 g. All individual plants were selected during the generation adding period, based on the criteria: strong boll formation, fiber length not less than 30 mm, lint percent not less than 38% per plant, and key screening for disease resistance and high temperature resistance during planting in Changde, Hunan. The breeding process was shown in Table 2.

TABLE 2

Breeding process of parent Xiang 267 line

| Time | Location | Breeding process | Breeding method |
|---|---|---|---|
| Winter 2007 | Sanya, Hainan | Xiangzamian No. 13 $F_1$ ↓ | |
| Spring 2008 | Changde, Hunan | Xiangzamian No. 13 $F_2$ sister line mixing ↓ | Mixing |
| Winter 2008 | Sanya, Hainan | Mixed $F_1$ ↓ | Individual plant selection |

TABLE 2-continued

Breeding process of parent Xiang 267 line

| Time | Location | Breeding process | Breeding method |
|---|---|---|---|
| Spring 2009 | Changde, Hunan | F2 ↓ | Individual plant selection |
| Winter 2009 | Sanya, Hainan | $F_3$ ↓ | Individual plant selection |
| Spring 2010 | Changde, Hunan | $F_4$ ↓ | Individual plant selection |
| Winter 2010 | Sanya, Hainan | $F_5$ ↓ | Individual plant selection |
| Spring 2011 | Changde, Hunan | $F_6$ (Xiang 267) | |

Step 3. Breeding:

In the before summer of 2011, the two-parent materials mutually acted as parents to prepare a reciprocal cross combination in Changde, Hunan, according to the material characteristics of Xiang 176 and Xiang 267 lines, combined with the breeding goal;

In winter of 2011, the reciprocal cross combination $F_1$ was planted in Sanya, Hainan, and was crossed (the quantitative traits of cotton were affected by cytoplasmic inheritance, and the traits of its progeny were partial to the female parent, so the reciprocal cross combination was composite-crossed to reduce the influence of cytoplasmic inheritance on the progeny and increase the probability of excellent gene recombination), to obtain composite cross $F_1$ seeds; From 2012 to the before spring of 2014, a generation was added in Changde, Hunan and Sanya, Hainan every year (5 generations in total, individual plants were selected based on the criteria: high yield, fiber length not less than 31 mm, lint percent not less than 40%, and key screening for disease resistance and high-temperature resistance during planting in Changde, Hunan), to obtain $F_6$ seeds;

In winter of 2014, $F_6$ strains were comparatively tested in Sanya, Hainan, to obtain 11 excellent $F_7$ strains;

In 2015, the 11 excellent $F_7$ strains were comparatively tested three times in Changde, Hunan, and the final strain was named Xiang X0935.

The Xiang X0935 had a high yield and excellent fiber quality. The seed test results in 2015 were: staple length 31.5 mm, micronaire value 4.7, specific strength 35.4 CN/Tex, boll weight 6.3 g, lint percent 40.10%, and seed index 10.8 g.

The new variety Xiang X0935 of high-quality conventional *Gossypium hirsutum* bred by the present invention had the characteristics of tower type, good growth vigor in the seedling stage and the boll opening stage, good uniformity, dense stem cilia, white anthers, smooth boll opening, stable agronomic traits, high yield, and excellent fiber quality.

The beneficial effects of the present invention will be described below in conjunction with experimental data:

The new variety Xiang X0935 of the present invention participated in the regional test of ordinary cotton varieties in Hunan in 2019, and the experimental process was as follows:

(1) Tested Varieties

A total of 6 cotton QA groups participated in the test, including 5 groups of hybrid cotton and 1 group of conventional cotton. Xiangzamian No. 7 was a control.

(2) Test Unit

A total of 5 test units: Yueyang City Junshan District Agricultural Science Research Institute, Li County Agricultural and Rural Bureau, Yiyang City Datonghu District Agricultural Technology Promotion Center, Hunnan Cotton Science Institute, and Nanxian Cotton Original Seed Farm.

The Nanxian Cotton Original Seed Farm failed in the test due to the weather, and its data was not included in the summary.

All other pilots completed the test according to the experimental plan, the plant shortage rate in the plots did not exceed 15%, the coefficient of variation of the pilot error did not exceed 15%, and the data were all included in the summary.

(3) Weather Conditions

The continuous overcast and rainy low-temperature weather after sowing had a certain impact on the emergence and growth of cotton seedlings. The emergence speed and uniformity were worse than in previous years. After transplanting, the temperature was slightly lower than in previous years, the light was reduced, the precipitation was more than in previous years, and the growth of cotton seedlings was worse than in previous years. The heavy rain in July had a certain impact on the budding and flowering of cotton. The temperature in August was lower than in previous years, the precipitation was higher than in previous years, and the growth of cotton was normal. In September, the temperature fluctuated greatly, the long-term overcast or rainy and scant lighting and drastic temperature changes caused serious shedding of cotton bolls, more rotten bolls and more dead cotton, and the quality of cotton was worse than in previous years. In October, the temperature tended to be normal, cotton grew well and bolls opened well.

(4) Quality and Stability Analysis

Quality: tested by the Cotton Quality Supervision, Inspection, and Testing Center of the Ministry of Agriculture. The test basis was GB/T20392-2006 HVI Cotton Fiber Physical Properties Test Method. Stability: the suitable planting environments of the tested varieties were evaluated with a regression coefficient this year. The analysis results of yield and stability of each variety were as follows.

(5) Yield and Stability Analysis

The lint yields per mu of the tested varieties were 105.3 to 116.3 kg, and the lint yield per mu of the control (CK, fiber quality type II) was 105.3 kg. After statistical analysis, MHQA3, MHQA2, MHQA4, MHQA1, and MHQA6 increased the yield significantly compared with the control, and no variety decreased the yield significantly compared with the control.

(6) Brief Introduction to the Growth Period

The average growth period of the tested varieties was 119.8 to 121.8 days, and the growth period of the control (CK) was 121 days.

2. Brief Review of the Combination

1. MHQA1: Xiang X0935, conventional cotton, continued trial combination, provided by Hunan Cotton Science Institute.

The results of the 2019 provincial test: the average growth period was 125.4 days, 3.0 days longer than the control. The lint yield per mu was 117.63 kg, an increase of 0.7 compared with the control, ranking second among the tested varieties, and the increase in yield was not significant. Two out of five pilots increased the yield. The plant height was 124.9 cm, the first fruiting site was 6.3 cm, the number of fruiting branches per plant was 18.8, the number of bolls formed per plant was 47.1, the number of bolls opened per plant was 42.9, the weight of the seed cotton per boll was 6.0 g, the rate of dead cotton was 0.9%, and the flowering rate before frosting was 99.0%. The lint percent was 41.2%, the seed index was 11.8 g, and the lint index was 7.9 g. The average length of the upper half was 32.1 mm, the uniformity index was 86.6%, the breaking strength was 39.0 CN/tex, the micronaire value was 4.7, the reflectance was 80.6%, the yellowness was 7.6, and the spinning uniformity index was 185.4. After identification, the relative disease index (IR) of fusarium wilt was 14.0, the average resistance grade of fusarium wilt was Disease Tolerance; the relative disease index (IR) of verticillium wilt was 21.9, the average resistance grade of verticillium wilt was Disease Tolerance.

The plant type of this variety was tower type, with good growth vigor in the seedling stage and the boll opening stage, good uniformity, dense stalk cilia, white anthers, and smooth boll opening. Fiber quality was type II, and the variety had a high lint yield.

The results of the 2020 provincial test: the average growth period was 121.5 days, 0.5 days longer than the control. The lint yield per mu was 110 kg, 4.4% higher than that of the control, ranking fourth among the tested varieties, and the yield increase was extremely significant. Three out of four pilots increased the yield. The plant height was 125.8 cm, the first fruiting site was 6.4 cm, the number of fruit branches per plant was 19.1, the number of bolls formed per plant was 47.5, the number of bolls opened per plant was 44.4, the weight of seed cotton per boll was 6.5 g, the rate of dead cotton was 6.7%, and the flowering rate before frosting was 97%. The lint percent was 41.2%, the seed index was 11.8 g, and the lint index was 7.8 g. The average length of the upper half was 31.9 mm, the uniformity index was 85.7%, the breaking strength was 35.2 CN/tex, the micronaire value was 4.2, the elongation was 5.7%, the reflectance was 80.9%, the yellowness was 7, and the spinning uniformity index was 173.3. The average resistance grade of verticillium wilt was Disease Tolerance, relative index (IR) of verticillium wilt was 24.4; average resistance grade of fusarium wilt was Disease Tolerance, relative index (IR) of fusarium wilt was 11.1.

The plant type of this variety was tower type, with strong growth vigor in the seedling stage and the boll opening stage, good uniformity, dense stalk cilia, white anthers, and smooth boll opening. Fiber quality was type I. The regional test was completed.

The average results of the two-year regional test: the growth period was 123.5 days, 1.6 days longer than the control. The lint yield per mu was 113.7 kg, 2.5% higher than that of the control. The plant height was 125.4 cm, the number of fruit branches per plant was 19.0, the number of bolls formed per plant was 43.6, the weight of seed cotton per boll was 6.2 g, the flowering rate before frosting was 98.0%, the lint percent was 41.2%, the seed index was 11.8 g, and the lint index was 7.8 g. The average length of the upper half was 32.0 mm, the specific strength was 37.1 CN/tex, the micronaire value was 4.5, the uniformity index was 86.2%, the spinning uniformity index was 179.4, and the cotton type was type II. The relative disease index (IR) of fusarium wilt was 12.6, the average resistance grade of fusarium wilt was Disease Tolerance; the relative disease index (IR) of verticillium wilt was 23.2, the average resistance grade of verticillium wilt was Disease Tolerance.

2. MHQA2: Nannong 995, continued test combination, provided by Nanjing Agricultural University.

The results of 2019 provincial test: the average growth period was 124.8 days, 2.4 days longer than the control. The lint yield per mu was 112.34 kg, 3.84% lower than that of the control, ranking fifth among the tested varieties, and the yield decrease was not significant. The plant height was 128.26 cm, the first fruiting site was 6.2 cm, the number of fruiting branches per plant was 18.28, the number of bolls formed per plant was 43.76, the number of bolls opened per plant was 39.86, the weight of seed cotton per boll was 6.24 g, the rate of dead cotton was 0.9%, and the flower rate before frosting was 98.88%. The lint percent was 41.36%, the seed index was 10.86 g, and the lint index was 7.28 g. The average length of the upper half was 28.3 mm, the uniformity index was 84.3%, the breaking strength was 29.7 CN/tex, the micronaire value was 5.1, the reflectance was 79.9%, the yellowness was 8.0, and the spinning uniformity index was 134.6. After identification, the relative disease index (IR) of fusarium wilt was 17.3, the average resistance grade of fusarium wilt was Disease Tolerance; the relative disease index (IR) of verticillium wilt was 22.9, the average resistance grade of verticillium wilt was Disease Tolerance.

The plant type of this variety was tower type, with good growth vigor in the seedling stage and the boll opening stage, good uniformity, dense stalk cilia, white anthers, and smooth boll opening. Fiber quality was type II, and the variety had a high lint yield.

The results of 2020 provincial test: the average growth period was 121.8 days, 0.8 days longer than the control. The lint yield per mu was 112 kg, 6.3% higher than that of the control, ranking second among the tested varieties, and the yield increase was extremely significant.

All of the four pilots increased the yield. The plant height was 127.2 cm, the first fruiting site was 6.4 cm, the number of fruit branches per plant was 18.8, the number of bolls formed per plant was 48, the number of bolls opened per plant was 43.6, the weight of seed cotton per boll was 6.4 g, the rate of dead cotton was 7.2%, and the flower rate before frosting was 96.7%. The lint percent was 42%, the seed index was 11.4 g, and the lint index was 7.9 g. The average length of the upper half was 28.2 mm, the uniformity index was 83.0%, the breaking strength was 28.5 CN/tex, the micronaire value was 4.8, the elongation was 5.5%, the reflectance was 78.4%, the yellowness was 8.3, and the spinning uniformity index was 126.5. Average resistance grade of verticillium wilt was Disease Resistance, relative index (IR) of verticillium wilt was 17.0; the average resistance grade of fusarium wilt was Disease Tolerance, relative index (IR) of fusarium wilt was 18.4.

The plant type of this variety was tower type, with strong growth vigor in the seedling stage and the boll opening stage, good uniformity, dense stalk cilia, white anthers, and smooth boll opening. Fiber quality was type III. The regional test was completed.

The average results of two-year regional test: the growth period was 123.3 days, 1.6 days longer than the control. The lint yield per mu was 112.2 kg, 5.1% higher than that of the control. The plant height was 127.7 cm, the number of fruit branches per plant was 18.5, the number of bolls formed per plant was 41.7, the weight of seed cotton per boll was 6.3 g, the flower rate before frosting was 97.8%, the lint percent was 41.7%, the seed index was 11.1 g, and the lint index was 7.6 g. The average length of the upper half was 28.2 mm, the specific strength was 29.1 CN/tex, the micronaire value was 4.9, the uniformity index was 83.6%, the spinning uniformity index was 130.6, and the cotton type was type III. The relative disease index (IR) of fusarium wilt was 17.9, the average resistance grade of fusarium wilt was Disease Tolerance; the relative disease index (IR) of verticillium wilt was 20.0, the average resistance grade of verticillium wilt was Disease Tolerance.

3. MHQA3: Xiang cotton 34, first test combination, provided by Hunan Cotton Research Institute.

The results of 2020 provincial test: the average growth period was 119.8 days, 1.2 days shorter than the control. The lint yield per mu was 116.3 kg, 10.4% higher than that of the control, ranking first among the tested varieties, and the yield increase was extremely significant. All of the four pilots increased the yield. The plant height was 127.5 cm, the first fruiting site was 6.4 cm, the number of fruit branches per plant was 19.4, the number of bolls formed per plant was 48.5, the number of bolls opened per plant was 43.9, the weight of seed cotton per boll was 6.1 g, the rate of dead cotton was 7.4%, and the flower rate before frosting was 96.7%. The lint percent was 43.6%, the seed index was 10.3 g, and the lint index was 7.8 g. The average length of the upper half was 29.5 mm, the uniformity index was 84.9%, the breaking strength was 30.8 CN/tex, the micronaire value was 4.8, the elongation was 5.4%, the reflectance was 79.8%, the yellowness was 8, and the spinning uniformity index was 145.8. Average resistance grade of verticillium wilt was Disease Tolerance, relative index (IR) of verticillium wilt was 34.8; average resistance grade of fusarium wilt was Disease Tolerance, relative index (IR) of fusarium wilt was 12.9.

The plant type of this variety was tower type, with strong growth vigor in the seedling stage and the boll opening stage, good uniformity, dense stalk cilia, white anthers, and smooth boll opening. Fiber quality was type II. The test of the variety was continued and the variety was performed production test.

4. MHQA4: Xiang cotton 32, first test combination, provided by Hunan Cotton Research Institute.

The results of 2020 provincial test: the average growth period was 120 days, 1 day shorter than the control. The lint yield per mu was 111.3 kg, 5.7% higher than that of the control, ranking third among the tested varieties, and the yield increase was extremely significant. All of the four pilots increased the yield. The plant height was 127.5 cm, the first fruiting site was 6.6 cm, the number of fruit branches per plant was 19.6, the number of bolls formed per plant was 49, the number of bolls opened per plant was 45.4, the weight of seed cotton per boll was 5.8 g, the rate of dead cotton was 7.2%, and the flower rate before frosting was 96.9%. The lint percent was 41.4%, the seed index was 10.5 g, and the lint index was 7.1 g. The average length of the upper half was 28.9 mm, the uniformity index was 84.7%, the breaking strength was 32.3 CN/tex, the micronaire value was 4.6, the elongation was 6.8%, the reflectance was 78.1%, the yellowness was 8, and the spinning uniformity index was 149.3. The average resistance grade of verticillium wilt was Disease Resistant, relative index (IR) of verticillium wilt was 19.4; average resistance grade of fusarium wilt was disease susceptible, relative index (IR) of fusarium wilt was 28.6.

The plant type of this variety was tower type, with strong growth vigor in the seedling stage and the boll opening stage, good uniformity, dense stalk cilia, white anthers, and smooth boll opening. Fiber quality was type II. The test was stopped.

5. MHQA6: Xiang Q190, first test combination, provided by Hunan Cotton Research Institute.

The results of 2020 provincial test: the average growth period was 120.2 days, 0.8 days shorter than the control. The lint yield per mu was 108.7 kg, 3.2% higher than that of the control, ranking fifth among the tested varieties, and the yield increase was extremely significant. All of the four pilots increased the yield. The plant height was 128.3 cm, the first fruiting site was 6.4 cm, the number of fruit branches per plant was 19, the number of bolls formed per plant was 47.4, the number of bolls opened per plant was 42.8, the weight of seed cotton per boll was 6.2 g, the rate of dead cotton was 7.3%, and the flower rate before frosting was 96.6%. The lint percent was 41.2%, the seed index was 11.6 g, and the lint index was 7.4 g. The average length of the upper half was 29.5 mm, the uniformity index was 84.4%, the breaking strength was 31.1 CN/tex, the micronaire value was 4.3, the elongation was 6%, the reflectance was 79.2%, the yellowness was 8, and the spinning uniformity index was 149. Average resistance grade of verticillium wilt was disease tolerance, the relative index (IR) of verticillium wilt was 30.9; average resistance grade of fusarium wilt was Disease Tolerance, relative index (IR) of fusarium wilt was 10.4.

The plant type of this variety was tower type, with strong growth vigor in the seedling stage and the boll opening stage, good uniformity, dense stalk cilia, white anthers, and smooth boll opening. Fiber quality was type II. The test of the variety was continued and the variety was performed production test.

The Hunan regional test showed that Xiang X0935 was conventional cotton, the control variety was hybrid cotton, and Xiang X0935 had an obvious advantage in increasing seed cotton yield and also increased the lint yield by 2.5% (national variety certification standard: the yield of conventional cotton was 5% lower than that of hybrid cotton of the same type). The fiber quality was excellent, the fiber length and strength reached the national variety certification type I standard, and the micronaire value reached the national variety certification type II standard. Under the high temperature climate in Hunan, the fiber maturity was too high, and the micronaire value performed well. In the past 10 years, there has been no medium-maturing variety approved with a micronaire value lower than 5.0 in Hunan.

The new variety Xiang X0935 of the present invention was tested in the regional test of medium-maturing cotton varieties in Jiangsu Province in 2020, and the experimental process was as follows:

1. Test Objective

By the principles of fairness, impartiality, science and efficiency, the differences between new varieties (lines) of cotton and controls in yield, stress resistance, adaptability, fiber quality, and comprehensive performance in cotton regions of Jiangsu Province were identified through multi-environmental experiments, to objectively evaluate the characteristics and production and utilization value of the tested varieties, to provide a scientific basis for the approval and promotion of cotton varieties in Jiangsu Province.

2. Test Materials

A total of 13 mid-maturing cotton varieties participated in the regional test, numbered A1 to A13, of which A3 and A13 were control varieties Siza No. 3 and Sikang No. 1 respectively. Yan G1601 and Zhongmiansuo 9702 were mid-maturing hybrid cotton varieties, with Siza No. 3 as the control; Huimian No. 1, Nannong 997, Xiang FZ031, Qingmian No. 1, Yanmian 118, Xiang X0935, Zhong MBC31123, Sumian 5042 and Xumian 399 were mid-maturing conventional cotton varieties, with Sikang No. 1 as the control. The conventional cotton varieties Xiang FZ031 and Qingmian No. 1 were tested in the second year, and the remaining varieties were tested in the first year. See Table 3 for names and types of tested varieties, test year and breeding units.

TABLE 3

Sources and types of mid-maturing cotton varieties tested in Jiangsu Province in 2020

| No. | Variety name | Variety type | Regional test year | Breeding (declaration) unit |
|---|---|---|---|---|
| A1 | Yan G1601 | Mid-maturing hybrid | First year | Jiangsu Coastal Area Agricultural Research Institute |
| A2 | Zhongmiansuo 9702 | Mid-maturing hybrid | First year | Cotton Research Institute of Chinese Academy of Agricultural Sciences |
| A3 | Siza No. 3 (CK) | Mid-maturing hybrid | Control | Siyang Cotton Original Farm |
| A4 | Huimian No. 1 | Mid-maturing conventional | First year | Cotton Research Institute of Anhui Academy of Agricultural Sciences |
| A5 | Nannong 997 | Mid-maturing conventional | First year | Nanjing Agricultural University |
| A6 | Xiang FZ031 | Mid-maturing conventional | Second year | Hunan Cotton Research Institute, Jiangsu Coastal Area Agricultural Research Institute |
| A7 | Qingmian No. 1 | Mid-maturing conventional | Second year | Cotton Research Institute of Anhui Academy of Agricultural Sciences, Jiangsu Coastal Area Agricultural Research Institute |
| A8 | Yanmian 118 | Mid-maturing conventional | First year | Jiangsu Coastal Area Agricultural Research Institute, Cotton Research Institute of Anhui Academy of Agricultural Sciences, Cotton Research Institute of Chinese Academy of Agricultural Sciences |
| A9 | Xiang X0935 | Mid-maturing conventional | First year | Hunan Cotton Research Institute |
| A10 | Zhong MBC31123 | Mid-maturing conventional | First year | Cotton Research Institute of Chinese Academy of Agricultural Sciences |
| A11 | Sumian 5042 | Mid-maturing conventional | First year | Economic Crops Research Institute of Jiangsu Academy of Agricultural Sciences |
| A12 | Xumian 399 | Mid-maturing conventional | First year | Xuzhou Institute of Agricultural Sciences, Xuhuai District, Jiangsu |
| A13 | Sikang No. 1 (CK) | Mid-maturing conventional | Control | Siyang Cotton Original Farm |

3. Overview of Test

In 2020, the field trials of group A were deployed in 9 sites across the province: Jiangsu Coastal Area Agricultural Science Institute (Yancheng), Yancheng Xinyang Agricultural Experiment Station (Xinyang), Jiangsu Golden Agriculture Co., Ltd. (Dafeng), Dongtai Municipal Institute of Agricultural Sciences (Dongtai), Liuhe Longpao Cotton Experiment Station (Liuhe), Yanjiang Institute of Agricultural Sciences (Nantong), Xinghua Yinhua Cotton Industry Co., Ltd. (Xinghua), Xuzhou Institute of Agricultural Sciences (Xuzhou), and Dongxin Farm Agricultural Research Institute (Dongxin). Nantong site was removed due to floods, while Dafeng and Xinghua sites increased the yield of conventional cotton varieties by more than 30% and did not participate in the summary; the remaining pilot sites were arranged in random blocks, repeated 3 times, the plot area was about 20 m², the plant and row spacing were configured to be reasonable, the plant shortage rate in the plots did not exceed 10%, the coefficient of variation of the pilot error did not exceed 10%, other conditions also met the requirements of the experimental plan, and all participated in the summary.

The tested varieties were entrusted to the Plant Protection Institute of Jiangsu Academy of Agricultural Sciences for cotton bollworm resistance identification and Verticillium wilt resistance inoculation identification, the Xuzhou Institute of Agricultural Sciences for field natural inoculation identification on Verticillium wilt resistance, the Cotton Quality Supervision and Testing Center of the Ministry of Agriculture for fiber quality test, the Institute of Biotechnology of the Chinese Academy of Agricultural Sciences for Bt insect-resistant protein test, and the Economic Crops Institute of Jiangsu Academy of Agricultural Sciences and the Dafeng Rice and Wheat Original Breeding Farm for salt-tolerance identification on conventional varieties.

4. Climate Characteristics and Cultivation Management During Cotton Growth and Development Period (1) Climate Characteristics The climate in the seedling stage of most of the pilots was good, which was favorable for the emergence and growth of cotton seedlings. The late seedling stage entered the plum rain period, the rainy season was relatively long and the rainfall was relatively large, which were extremely unfavorable for the growth and early development of cotton seedlings. From the end of the plum rain period in the late budding and bolling stage to the boll opening stage, the weather was fine, and the light and temperature conditions were suitable, which were favorable for the opening and harvesting of cotton bolls.

Seedling stage: after sowing, the weather in most of the pilots was fine and the temperature was relatively high, which was favorable for seedling emergence; the cotton seedlings were tidy and grew well; Dongxin had more rainfall and insufficient light, which was unfavorable for the emergence and growth of cotton seedlings; the Xuzhou pilot was relatively arid, which was unfavorable for the growth of cotton seedlings; the Dafeng and Nantong pilots had a dry climate in early June, so cotton grew slowly; the Liuhe and Yancheng pilots entered the plum rain season in the middle of June, and the overcast and rainy weather continued, which were unfavorable for the growth of cotton.

Budding and bolling stage: most of the pilots had a relatively long plum rain period and relatively large rainfall this year, and the continuous overcast and rainy weather in the early budding and bolling stage was extremely unfavorable for the growth and development of cotton; after the plum rain period, the fine weather, high temperature and sufficient light were favorable for the growth, flowering and bolling of cotton.

Boll opening stage: in the boll opening stage, each pilot had suitable light and temperature conditions and a little rainfall, which was favorable for boll formation, boll opening and harvesting of cotton; the Xinyang pilot had more overcast and rainy weather in the early boll opening stage, which was unfavorable for the opening of cotton bolls, and there were more rotten bolls at the lower part; the Xinghua pilot had a lot of rain in late November, which was unfavorable for boll opening and picking in late autumn.

(2) Cultivation Management

The predecessors of the experimental plots were mainly idle fields in winter, the preceding cropin Xinghua was strawberry, the preceding crop in Dafeng was barley green manure, and the predecessors in other pilots were idle fields in winter. The soil types were mainly loam and clay, with 3 pilots for sandy loam and clay, 1 for tidal saline soil, and 1 for mixed soil. 5 pilots adopted seedling transplantation, and 3 pilots adopted direct sowing with mulching films. The sowing period varied from April 8 to April 27, where early April in the Yancheng pilot, late April in Dongxin pilot, and mid-April was in other pilots. The transplantation period varied from May 6 to May 28, where May 6 in Liuhe pilot, May 28 in Xinghua, and mid-May in other pilots.

According to the fertility of the experimental plots and the growth vigor and appearance of cotton, different quantities of organic fertilizers and chemical fertilizers were applied to the pilots during basal application and dressing. The nitrogen fertilizer mainly included urea, the phosphate fertilizer mainly included superphosphate and diammonium phosphate, and the potash fertilizer mainly included potassium chloride, potassium sulfate, and a ternary compound fertilizer of nitrogen, phosphorus and potassium. The organic fertilizers were mainly organic and inorganic compound fertilizers. Chemical control of pests and diseases was performed on average 11 times, and the main pests were: lygus bug, cotton bollworm, red spider, aphids, *Spodoptera litura*, etc. In each pilot, the average cultivating and weeding were performed 3.4 times, pruning was performed 3 times, chemical adjustment was performed 3.8 times, and the topping stage was from August 1 to August 15.

5. Test Results

A "crop regional test management system" was used for variance analysis and multiple comparisons on lint yield data of various varieties in the test.

(1) Yielding Ability

1. Yield Level

The yielding abilities of the tested varieties in 2020 were as follows (Table 4): (1) among the hybrid cotton varieties, the yields of unginned cotton and ginned cotton of Yan G1601 increased by 12.4% and 14.9% respectively compared with the control variety Siza No. 3; and the yields of unginned cotton and ginned cotton of Zhongmiansuo 9702 decreased by 1.7% and 5.6% respectively compared with the control variety Siza No. 3. (2) Among the conventional cotton varieties, the yield of unginned cotton of Xiang X0935 increased by more than 10% compared with the control Sikang No. 1; the yields of unginned cotton of Sumian 5042, Xiang FZ031, Huimian No. 1, Qingmian No. 1, Xumian 399 and Nannong 997 increased by more than 5% compared with the control; the yield of Yanmian 118 increased by more than 3.0%; and the yield of unginned cotton of Zhong MBC31123 decreased by 0.9% compared with the control Sikang No. 1. The yield of ginned cotton of Xiang X0935 increased by more than 10% compared with the control Sikang No. 1; the yields of ginned cotton of Sumian 5042, Huimian No. 1, Qingmian No. 1, Xumian 399 and Xiang FZ031 increased by more than 5% compared with the control; the yield of Yanmian 118 increased by more than 3.0%, and the yield of ginned cotton of Zhong MBC31123 decreased by 6.2% compared with the control Sikang No. 1.

The average yields of the tested varieties from 2019 to 2020 were as follows (Table 4): the yields of unginned cotton and ginned cotton of Xiang FZ031 increased by 6.6% and 2.7% respectively compared with the control Sikang No. 1; and the yields of unginned cotton and ginned cotton of Qingmian No. 1 increased by 6.3% and 7.9% respectively compared with the control Sikang No. 1.

TABLE 4

Summary of regional test yields of medium-maturing cotton varieties in Jiangsu Province in 2020

| No. | Variety name | Year | Yield of unginned cotton | | | Yield of ginned cotton | | | Flower rate before frosting (%) | Lint percent (%) |
|-----|--------------|------|-------|------|------|-------|------|------|------|------|
| | | | kg/mu | ck % | rank | kg/mu | ck % | Rank | | |
| A01 | Yan G1601 | 2020 | 290.9 | 112.4 | 1 | 120.3 | 114.9 | 1 | 88.8 | 41.3 |
| A02 | Zhongmiansuo | 2020 | 254.5 | 98.3 | 3 | 98.9 | 94.4 | 3 | 84.9 | 38.9 |
| A03 | Siza No. 3 | 2020 | 258.8 | 100.0 | 2 | 104.7 | 100.0 | 2 | 87.1 | 40.6 |
| A04 | Huimian No. 1 | 2020 | 258.8 | 108.1 | 5 | 107.5 | 109.4 | 3 | 91.0 | 41.6 |
| A05 | Nannong 997 | 2020 | 251.7 | 105.1 | 7 | 100.1 | 101.9 | 8 | 91.0 | 39.7 |
| A06 | Xiang FZ031 | 2019 | 269.0 | 104.4 | 4 | 107.1 | 99.0 | 7 | 96.0 | 40.0 |
| A06 | Xiang FZ031 | 2020 | 260.6 | 108.8 | 3 | 104.5 | 106.4 | 6 | 93.6 | 40.1 |
| A06 | Xiang FZ031 | Two years | 264.8 | 106.6 | | 105.8 | 102.7 | | 94.8 | 40.1 |
| A07 | Qingmian No. 1 | 2019 | 269.0 | 104.4 | 3 | 115.3 | 106.6 | 3 | 94.2 | 42.9 |
| A07 | Qingmian No. 1 | 2020 | 258.9 | 108.1 | 4 | 107.2 | 109.1 | 4 | 90.3 | 41.2 |
| A07 | Qingmian No. 1 | Two years | 264.0 | 106.3 | | 111.2 | 107.9 | | 92.2 | 42.1 |
| A08 | Yanmian 118 | 2020 | 248.4 | 103.7 | 8 | 102.7 | 104.6 | 7 | 89.2 | 41.3 |
| A09 | Xiang X0935 | 2020 | 274.5 | 114.6 | 1 | 110.0 | 111.9 | 1 | 92.6 | 40.1 |
| A10 | Zhong MBC31123 | 2020 | 237.2 | 99.1 | 10 | 92.2 | 93.8 | 10 | 90.3 | 38.9 |
| A11 | Sumian 5042 | 2020 | 263.2 | 109.9 | 2 | 107.8 | 109.7 | 2 | 92.1 | 41.0 |
| A12 | Xumian 399 | 2020 | 254.3 | 106.2 | 6 | 107.0 | 108.9 | 5 | 90.9 | 42.0 |
| A13 | Sikang No. 1 | 2019 | 257.5 | 100.0 | 7 | 108.1 | 100.0 | 6 | 93.7 | 42.1 |

TABLE 4-continued

Summary of regional test yields of medium-maturing cotton varieties in Jiangsu Province in 2020

| No. | Variety name | Year | Yield of unginned cotton kg/mu | ck % | rank | Yield of ginned cotton kg/mu | ck % | Rank | Flower rate before frosting (%) | Lint percent (%) |
|---|---|---|---|---|---|---|---|---|---|---|
| A13 | Sikang No. 1 | 2020 | 239.5 | 100.0 | 9 | 98.2 | 100.0 | 9 | 90.5 | 41.1 |
| A13 | Sikang No. 1 | Two years | 248.5 | 100.0 | | 103.2 | 100.0 | | 92.1 | 41.6 |

2. Joint Variance Analysis Results

The variance analysis results showed (Table 5-1 and Table 5-2; hybrid cotton and conventional cotton varieties in a group for the test were compared separately): the variety effect reached a very significant level, indicating that the differences between varieties were significant, and multiple comparisons between varieties were required.

The results of multiple comparisons between varieties were (Table 6): (1) among the hybrid cotton varieties, the yield of Yan G1601 increased significantly compared with the control Siza No. 3, and the yield of Zhongmiansuo 9702 decreased significantly compared with the control. (2) Among the conventional cotton varieties, the yields of Xiang X0935, Sumian 5042, Huimian No. 1, Qingmian No. 1, Xumian 399, Xiang FZ031 and Yanmian 118 increased significantly compared with the control, the yield of Nannong 997 did not increase significantly, and the yield of Zhong MBC31123 decreased significantly compared with the control.

TABLE 5-1

Table of variance analysis on lint yield in regional trials of mid-maturing cotton varieties in Jiangsu Province in 2020

| Source of variation | Degree of freedom | Sum of square | Mean square | F value | P value |
|---|---|---|---|---|---|
| Pilot block | 16 | 0.845 | 0.053 | 2.888 | 0.005 |
| Variety | 2 | 5.317 | 2.658 | 145.306 | 0.000 |
| Pilot | 7 | 23.091 | 3.299 | 180.309 | 0.000 |
| Variety × pilot | 14 | 1.845 | 0.132 | 7.205 | 0.000 |
| Error | 32 | 0.585 | 0.018 | | |
| Total variation | 71 | 31.683 | | | |

Note:
error coefficient of variation CV = 4.176%

TABLE 5-2

Table of variance analysis on lint yield in regional trials of mid-maturing cotton varieties in Jiangsu Province in 2020

| Source of variation | Degrees of freedom | Sum of square | Mean square | F value | P value |
|---|---|---|---|---|---|
| Pilot block | 12 | 0.171 | 0.014 | 0.906 | 0.544 |
| Variety | 9 | 4.392 | 0.488 | 30.975 | 0.000 |
| Pilot | 5 | 81.269 | 16.254 | 1031.739 | 0.000 |
| Variety × pilot | 45 | 6.166 | 0.137 | 8.697 | 0.000 |
| Error | 108 | 1.701 | 0.016 | | |
| Total variation | 179 | 93.699 | | | |

Note:
error coefficient of variation CV = 4.034%

TABLE 6

Difference significance test of lint yield in regional trials of mid-maturing cotton varieties in Jiangsu Province in 2020

| No. | Variety | Lint yield in plot (kg, 20 m$^2$) | 0.05 significance | 0.01 significance |
|---|---|---|---|---|
| A01 | Yan G1601 | 3.610 | a | A |
| A03 | Siza No. 3 (CK) | 3.140 | b | B |
| A02 | Zhongmiansuo 9702 | 2.966 | c | C |
| A09 | Xiang X0935 | 3.299 | a | A |
| A11 | Sumian 5042 | 3.233 | ab | AB |
| A04 | Huimian No. 1 | 3.223 | ab | AB |
| A07 | Qingmian No. 1 | 3.216 | abc | AB |
| A12 | Xumian 399 | 3.210 | bc | AB |
| A06 | Xiang FZ031 | 3.135 | cd | BC |
| A08 | Yanmian 118 | 3.081 | de | CD |
| A05 | Nannong 997 | 3.002 | ef | DE |
| A13 | Sikang No. 1 (CK) | 2.947 | f | E |
| A10 | Zhong MBC31123 | 2.764 | g | F |

Note:
LSD 0.05 = 0.0797;
LSD 0.01 = 0.1070 (hybrid group)
LSD 0.05 = 0.0833;
LSD 0.01 = 0.1100 (conventional group)

(2) Disease Resistance

In 2020, the tested varieties were entrusted to the Institute of Plant Protection, Jiangsu Academy of Agricultural Sciences to identify the resistance to fusarium wilt by means of bacteria soil at the seedling stage in a greenhouse, and the resistance to verticillium wilt by irrigating roots with a bacteria solution at the seedling stage in a greenhouse.

Identification of fusarium wilt: the inoculated strain was fusarium wilt Fnj (a highly pathogenic strain in Nanjing, preserved by the Plant Protection Institute of Jiangsu Academy of Agricultural Sciences), which was cultured in a Chapek liquid medium for 5-7 days while shaking, and then inoculated into a sterilized strain bag filled with wheat grains. After being cultured for 20 days, the wheat grains were taken out and dried. Then the wheat grains were mixed with sterilized nutrient soil at a percentage of 3%, and the mixture was put in a 16-hole plug tray (with 6.5 cm×6.5 cm×8.5 cm holes and a 32 cm×23 cm×3 cm plastic porcelain tray underlying). The tested varieties were planted in bacteria soil of greenhouse plug trays, and each variety was planted in 1 tray, repeated 3 times. After emergence, 32 seedlings were left in each tray. Seeds were sowed on April 14, and seedlings were finally singled on April 30. Simian No. 2 was a susceptible control, and Zhongzhimian No. 2 was a resistant control.

Identification on verticillium wilt: the inoculated strain of verticillium wilt nursery was V08DF-1 (Dafeng strong pathogenic deciduous type strain, preserved by the Plant Protection Institute of Jiangsu Academy of Agricultural Sciences). The strain was cultured in a potato liquid medium for 7 days while shaking, the cultured bacteria solution was inoculated into a sterilized wheat grain medium and cultured at 25° C. for 30 days, and after mycelia were full, wheat grains were taken out and dried in the air under natural conditions for later use. In the new disease nursery, the cultured wheat grain strains were uniformly applied to the field according to the inoculation amount of 450-750 Kg per hectare, and then the field was plowed 2-3 times to mix germs with soil uniformly. Specifically, each cement pond was uniformly inoculated with 2 kg of diseased wheat grains, which were uniformly applied to the field on March 23 and April 16 respectively before plowed. On April 30, each row was inoculated with 30 g of diseased wheat grains for booster inoculation. Proper humidity was maintained in the field to facilitate the occurrence of diseases. The tested varieties were randomly arranged, sown on April 30, 1 row per variety, repeated twice, and seedlings were finally singled on June 12. Simian No. 3 was a susceptible control, and Zhongzhimian No. 2 was a resistant control.

According to the relative resistance index (IR) of each variety, the disease resistance was divided into five grades: I (immune), HR (high resistant), R (resistant), T (tolerant) and S (susceptible). The grading criteria for disease resistance were:

Disease resistance grades: I (immune) HR (high resistant) R (resistant) T (tolerant) S (susceptible)

Fusarium wilt (IR): 0.0 0.1-5.0 5.1-10.0 10.1-20.0 ≥20.1

Verticillium wilt (IR): 0.0 0.1-10.0 10.1-20.0 20.1-35.0 ≥35.1

1. Identification results of fusarium wilt and verticillium wilt in Nanjing disease nurseries Inoculation identification results in 2020: Zhongmiansuo 9702 and Siza No. 3 (CK) were resistant to fusarium wilt and tolerant to verticillium wilt; Sumian 5042 was tolerant to fusarium wilt and resistant to verticillium wilt; and the rest of the tested varieties were tolerant to fusarium wilt and verticillium wilt.

Identification results of the tested varieties from 2019 to 2020 (Table 7): Xiang FZ031 and Qingmian No. 1 were both tolerant to fusarium wilt and verticillium wilt.

2. Identification results of verticillium wilt in Xuzhou natural disease nurseries Identification results of natural inoculation in 2020: Zhong MBC31123 and Yanmian 118 were highly resistant to verticillium wilt; Sikang No. 1 (CK), Xumian 399 and Qingmian No. 1 were resistant to verticillium wilt; Zhongmiansuo 9702, Siza No. 3 (CK), Nannong 997, Huimian No. 1 and Nannong 991 were tolerant to verticillium wilt; and Xiang FZ031, Yan G1601, Sumian 5042 and Xiang X0935 were susceptible to verticillium wilt.

Identification results of natural inoculation from 2019 to 2020: both Xiang FZ031 and Qingmian No. 1 were susceptible to verticillium wilt.

TABLE 7

Identification results of disease resistance in regional trials of mid-maturing cotton varieties in Jiangsu Province in 2020

| No. | Variety name | Year | Fusarium wilt Disease index | Fusarium wilt Resistance grade | Verticillium wilt Disease index | Verticillium wilt Resistance grade | Xuzhou greensickness Disease index | Xuzhou greensickness Resistance grade |
|---|---|---|---|---|---|---|---|---|
| A01 | Yan G1601 | 2020 | 16.0 | T | 22.4 | T | 41.7 | S |
| A02 | Zhongmiansuo 9702 | 2020 | 9.8 | R | 21.5 | T | 21.5 | T |
| A03 | Siza No. 3 | 2020 | 8.2 | R | 23.3 | T | 26.2 | T |
| A04 | Huimian No. 1 | 2020 | 15.4 | T | 33.0 | T | 28.3 | T |
| A05 | Nannong 997 | 2020 | 11.9 | T | 32.7 | T | 28.2 | T |
| A06 | Xiang FZ031 | 2019 | 9.8 | R | 22.3 | T | 41.4 | S |
| A06 | Xiang FZ031 | 2020 | 18.2 | T | 26.6 | T | 41.5 | S |
| A06 | Xiang FZ031 | Two years | 18.2 | T | 26.6 | T | 41.5 | S |
| A07 | Qingmian No. 1 | 2019 | 8.0 | R | 23.9 | T | 45.9 | S |
| A07 | Qingmian No. 1 | 2020 | 13.1 | T | 27.8 | T | 19.6 | R |
| A07 | Qingmian No. 1 | Two years | 13.1 | T | 27.8 | T | 45.9 | S |
| A08 | Yanmian 118 | 2020 | 13.2 | T | 22.5 | T | 7.8 | HR |
| A09 | Xiang X0935 | 2020 | 19.6 | T | 33.1 | T | 52.5 | S |
| A10 | Zhong MBC31123 | 2020 | 14.3 | T | 28.4 | T | 7.0 | HR |
| A11 | Sumian 5042 | 2020 | 14.6 | T | 18.2 | R | 49.1 | S |
| A12 | Xumian 399 | 2020 | 16.2 | T | 25.1 | T | 17.6 | R |
| A13 | Sikang No. 1 | 2019 | 9.7 | R | 20.6 | T | 36.5 | S |
| A13 | Sikang No. 1 | 2020 | 12.8 | T | 26.0 | T | 17.2 | R |
| A13 | Sikang No. 1 | Two years | 12.8 | T | 26.0 | T | 36.5 | S |

(4) Insect Resistance

In 2020, the Plant Protection Institute of the Jiangsu Academy of Agricultural Sciences conducted biological identification of the tested varieties against cotton bollworm, and the Institute of Biotechnology of the Chinese Academy of Agricultural Sciences tested Bt insect-resistant protein.

1. Biological Identification of Cotton Bollworm Resistance

Identification results in 2020 (Table 8): Zhong MBC31123, Sikang No. 1 (CK), Xumian 399, Qingmian No. 1, Zhongmiansuo 9702, Huimian No. 1, Xiang FZ031, and Sumian 5042 were all highly resistant to bollworm; and Yanmian 118, Siza No. 3 (CK), Nannong 997, Yan G1601 and Xiang X0935 were all resistant to cotton bollworm.

Two-year identification results from 2019 to 2020 (Table 8): Xiang FZ031 and Qingmian No. 1 were resistant to cotton bollworm.

2. Test on Bt Insect-Resistant Protein

The resistance grade indicated the level of toxic protein content, and the insect-resistant strain rate indicated whether there were non-insect-resistant strains.

Test results of Bt insect-resistant protein of the tested varieties in 2020 (Table 8): the insect-resistant strain rates of all tested varieties were above 90%, whereas the insect-resistant strain rates of Zhong MBC31123, Sikang No. 1 (CK), Xumian 399, Zhongmiansuo 9702, Sumian 5042, Yanmian 118, Siza No. 3 (CK), Nannong 997 and Xiang X0935 were all 100%; and the insect-resistant strain rates of Qingmian No. 1, Huimian No. 1, Yan G1601 and Xiang FZ031 were all above 90%, but still mixed with a few non-insect-resistant strains.

Test results of Bt insect-resistant protein from 2019 to 2020: the insect-resistant strain rates of Xiang FZ031 and Qingmian No. 1 were both above 90%, but still mixed with a few non-insect-resistant strains.

Zhongmiansuo 9702, Sikang No. 1 (CK), Zhong MBC31123, Siza No. 3 (CK), Nannong 997 and Xiang FZ031 were more than 29 mm, reaching the type II standard of ordinary high-quality cotton. The fiber lengths of Sumian 5042, Yanmian 118, Yan G1601, Huimian No. 1 and Xumian 399 were more than 27 mm, reaching the type III standard.

(2) Specific strength: the specific strengths of Zhongmiansuo 9702, Xiang X0935, Zhong MBC31123, Sikang No. 1 (CK), Nannong 997 and Siza No. 3 (CK) were more than 32 cN/tex, reaching the type I standard of high-quality cotton; and the specific strengths of the rest varieties all reached the type II standard.

(3) Micronaire value: the micronaire values of Xiang X0935, Zhongmiansuo 9702, Xiang FZ031, Qingmian No. 1 and Sikang No. 1 (CK) were less than 5.0, reaching the type II standard of ordinary high-quality cotton; the micronaire values of Nannong 997, Siza No.

TABLE 8

Identification results of cotton bollworm resistance in regional trials of mid-maturing cotton varieties in Jiangsu Province in 2020

| No. | Variety | Year | Test on Bt insect-resistant protein | | Biological identification of cotton bollworm resistance | | |
|---|---|---|---|---|---|---|---|
| | | | Insect-resistant strain rate (%) | Yes/No ≥90% | Comprehensive resistance value | Average resistance grade (PK) | Comprehensive resistance grade |
| A01 | Yan G1601 | 2020 | 96 | Yes | 40 | 3.3 | R |
| A02 | Zhongmiansuo 9702 | 2020 | 100 | Yes | 46 | 3.8 | HR |
| A03 | Siza No. 3 | 2020 | 100 | Yes | 41 | 3.4 | R |
| A04 | Huimian No. 1 | 2020 | 96 | Yes | 44 | 3.7 | HR |
| A05 | Nannong 997 | 2020 | 100 | Yes | 39 | 3.3 | R |
| A06 | Xiang FZ031 | 2019 | 96 | Yes | 31 | 2.6 | R |
| A06 | Xiang FZ031 | 2020 | 94 | Yes | 46 | 3.8 | HR |
| A06 | Xiang FZ031 | Two years | 94 | Yes | 31 | 2.6 | R |
| A07 | Qingmian No. 1 | 2019 | 98 | Yes | 38 | 3.2 | R |
| A07 | Qingmian No. 1 | 2020 | 98 | Yes | 45 | 3.8 | HR |
| A07 | Qingmian No. 1 | Two years | 98 | Yes | 38 | 3.2 | R |
| A08 | Yanmian 118 | 2020 | 100 | Yes | 38 | 3.2 | R |
| A09 | Xiang X0935 | 2020 | 100 | Yes | 33 | 2.8 | R |
| A10 | Zhong MBC31123 | 2020 | 100 | Yes | 44 | 3.7 | HR |
| A11 | Sumian 5042 | 2020 | 100 | Yes | 47 | 3.9 | HR |
| A12 | Xumian 399 | 2020 | 100 | Yes | 43 | 3.6 | HR |
| A13 | Sikang No. 1 | 2019 | 100 | Yes | 35 | 2.9 | R |
| A13 | Sikang No. 1 | 2020 | 100 | Yes | 43 | 3.6 | HR |
| A13 | Sikang No. 1 | Two years | 100 | Yes | 35 | 2.9 | R |

(5) Fiber Quality

The fiber qualities of the tested varieties were tested using the HVI900 system in the Cotton Quality Supervision, Inspection and Testing Center of the Ministry of Agriculture. The test and the humidity conditioning of cotton samples were carried out under the condition of a standard atmosphere (temperature 20±2° C., relative humidity 65±3%).

The average performance of the fiber quality of the tested varieties in 2020 was shown in Table 9: the uniformity indexes of all the tested varieties were more than 83%, all reaching the standard of high-quality cotton type I. Length, specific strength and micronaire values were as follows:

(1) Length: the fiber length of Xiang X0935 was more than 31 mm, reaching the type I standard of high-quality cotton; and the fiber lengths of Qingmian No. 1, 3 (CK), Huimian No. 1, Zhong MBC31123, Yanmian 118, Yan G1601 and Xumian 399 were between 5.1 and 5.5, belonging to type III; and the micronaire value of Sumian 5042 was 5.7, which did not reach the type III standard.

(4) Comprehensive evaluation: Xiang X0935, Zhongmiansuo 9702, Xiang FZ031, Qingmian No. 1 and Sikang No. 1 (CK) had good comprehensive performance in the three indexes, all reaching the ordinary high-quality type II standard; Nannong 997, Siza No. 3 (CK), Huimian No. 1, Zhong MBC31123, Yanmian 118, Yan G1601 and Xumian 399 had good comprehensive performance, all reaching the type III standard; and Sumian 5042 did not reach the type III standard due to its high micronaire value.

Performance of the tested varieties from 2019 to 2020: Xiang FZ031 and Qingmian No. 1 had good comprehensive performance in the three indexes, all reaching the ordinary high-quality type II standard.

TABLE 9

Fiber quality test results in regional trials of mid-maturing cotton varieties in Jiangsu Province in 2020

| No. | Variety name | Year | Staple length (mm) | Specific strength cN/tex | Micronaire value | Elongation (%) | Reflectance (%) | Yellowness | Uniformity (%) | Spinning index |
|---|---|---|---|---|---|---|---|---|---|---|
| A01 | Yan G1601 | 2020 | 28.7 | 31.0 | 5.4 | 7.1 | 77.8 | 8.3 | 84.9 | 138 |
| A02 | Zhongmiansuo 9702 | 2020 | 30.3 | 36.1 | 4.8 | 5.8 | 79.6 | 7.5 | 86.5 | 171 |
| A03 | Siza No. 3 | 2020 | 29.6 | 32.0 | 5.2 | 6.3 | 77.8 | 8.3 | 84.4 | 142 |
| A04 | Huimian No. 1 | 2020 | 28.1 | 30.8 | 5.2 | 5.6 | 78.9 | 8.0 | 84.3 | 136 |
| A05 | Nannong 997 | 2020 | 29.5 | 32.2 | 5.1 | 6.6 | 75.7 | 8.4 | 84.6 | 144 |
| A06 | Xiang FZ031 | 2019 | 30.2 | 29.7 | 4.6 | 6.9 | 82.0 | 7.8 | 85.5 | 151 |
| A06 | Xiang FZ031 | 2020 | 29.4 | 30.5 | 4.8 | 6.4 | 80.1 | 7.4 | 85.1 | 145 |
| A06 | Xiang FZ031 | Two years | 29.8 | 30.1 | 4.7 | 6.6 | 81.0 | 7.6 | 85.3 | 148 |
| A07 | Qingmian No. 1 | 2019 | 31.4 | 29.8 | 5.2 | 6.6 | 79.9 | 8.2 | 85.3 | 146 |
| A07 | Qingmian No. 1 | 2020 | 30.5 | 30.4 | 4.9 | 6.1 | 76.7 | 8.4 | 84.9 | 144 |
| A07 | Qingmian No. 1 | Two years | 30.9 | 30.1 | 5.0 | 6.4 | 78.3 | 8.3 | 85.1 | 145 |
| A08 | Yanmian 118 | 2020 | 28.8 | 31.1 | 5.3 | 5.8 | 79.2 | 7.8 | 85.0 | 141 |
| A09 | Xiang X0935 | 2020 | 32.2 | 35.9 | 4.6 | 5.5 | 80.2 | 7.1 | 85.9 | 173 |
| A10 | Zhong MBC31123 | 2020 | 29.9 | 34.8 | 5.3 | 5.3 | 79.6 | 7.3 | 85.1 | 154 |
| A11 | Sumian 5042 | 2020 | 28.9 | 31.5 | 5.7 | 6.3 | 77.1 | 8.3 | 83.9 | 133 |
| A12 | Xumian 399 | 2020 | 27.6 | 30.9 | 5.4 | 6.3 | 77.8 | 8.3 | 83.6 | 130 |
| A13 | Sikang No. 1 | 2019 | 30.2 | 31.1 | 5.1 | 6.1 | 79.6 | 8.3 | 84.7 | 144 |
| A13 | Sikang No. 1 | 2020 | 30.2 | 32.5 | 5.0 | 5.6 | 78.9 | 8.0 | 84.6 | 149 |
| A13 | Sikang No. 1 | Two years | 30.2 | 31.8 | 5.1 | 5.9 | 79.3 | 5.2 | 84.7 | 147 |

6. Conclusion

Xiang X0935 was a mid-maturing insect-resistant conventional cotton variety bred by Hunnan Cotton Science Institute and was tested in the first year. Regional test results in 2020: the growth period of spring sowing in cotton regions in Jiangsu Province was 130 days. The plant shape was relatively compact, the plant height was 105.2 cm, the fruit branches were long and flat, the stems were thick, the fuzz was less, the leaves were medium in size and dark in color, the first fruiting site was the 7th node, 29.1 bolls were formed per plant, the bolls were oval, the weight of a single boll was 6.5 g, the lint percent was 40.1%, the seed index was 12.9 g, the flowering rate before frosting was 92.6%, and the dead cotton rate was 4%.

The cotton had good seedling emergence, strong growth, good uniformity, no premature senescence, smooth boll opening, tolerant to fusarium wilt (fusarium wilt index 19.6), tolerant to verticillium wilt (verticillium wilt index 33.1), and resistance to cotton bollworm. The average length of the upper half of HVICC fibers was 32.2 mm, the specific strength at break was 35.9 cN/tex, the micronaire value was 4.6, the elongation at break was 5.5%, the reflectance was 80.2%, the yellow depth was 7.1, the uniformity index was 85.9%, and the spinning uniformity index was 173. The yields of unginned cotton, ginned cotton, and ginned cotton before frosting per mu were respectively 274.5 kg, 110 kg and 101.5 kg, which were respectively 114.6%, 111.9% and 114.6% of the control Sikang No. 1. Compared with the control, the yield increase advantage was extremely obvious and the quality was high.

The invention claimed is:

1. A method for breeding a new variety of *Gossypium hirsutum*, comprising the following steps:
    a) crossing a medium-long-staple Acala cotton line and a variety Xiangmian No. 18 as parents to obtain reciprocal cross $F_1$ combination seeds; then planting the reciprocal cross $F_1$ combination seeds in Hainan, and performing composite crossing to obtain composite cross $F_1$ seeds; in next 2 years, performing generation-adding planting of the composite cross $F_1$ seeds once in Changde, Hunan in summer and in Sanya, Hainan in winter each year, for a total of 4 generations, to obtain $F_5$ seeds; selecting from individual plants of the $F_5$ seeds in Changde, for fiber length not less than 32 mm, and lint percent not less than 45%, to obtain a strain a);
    b) mixing $F_2$ of existing approved variety Xiangzamian No. 13 to obtain mixed $F_1$ seeds, performing generation-adding planting on the mixed $F_1$ seeds in Changde, Hunan in summer and in Sanya, Hainan in winter each year, for a total of 5 generations, to obtain $F_6$ seeds, and selecting from the $F_6$ generation for fiber length not less than 30 mm, lint percent not less than 38% per plant to obtain a strain b); and c) crossing the strain a) and the strain b) as parents to obtain reciprocal cross $F_1$ seeds, then performing composite crossing on the reciprocal cross $F_1$ seeds to obtain composite cross $F_1$ seeds, performing generation-adding planting in Changde, Hunan in summer and in Sanya, Hainan in winter each year, continuously adding generations, and selecting individual plants from the $F_7$ generation exhibiting a higher yield compared to variety Sikang No. 1, fiber length not less than 31 mm, and lint percent not less than 40%.

2. The method of claim 1, wherein in the step a), the strain a) has a staple length of 32.9 mm, a micronaire value of 4.6, a specific strength of 36.5 CN/Tex, a boll weight of 6.5 g, a lint percent of 40.6%, and a seed index of 10.6 g; and the medium-long-staple Acala cotton line has a low lint percent of about 38%.

3. The method of claim 1, wherein in step b) the strain b) has a staple length of 32.9 mm, a micronaire value of 4.6, a specific strength of 36.5 CN/Tex, a boll weight of 6.5 g, a lint percent of 40.6%, and a seed index of 10.6 g.

4. The method of claim 2, wherein in step b) the strain b) has a staple length of 32.9 mm, a micronaire value of 4.6, a specific strength of 36.5 CN/Tex, a boll weight of 6.5 g, a lint percent of 40.6%, and a seed index of 10.6 g.

5. The method of claim 1, wherein in step c) individual plants from the $F_7$ generation are selected for a higher yield compared to variety Sikang No. 1, for a fiber length of not less than 31 mm and a lint percent not less than 40%.

6. The method of claim 5, that provides a variety having a micronaire value of 4.7, a specific strength of not less than 35 CN/Tex and a boll weight of not less than 6 grams.

\* \* \* \* \*